United States Patent [19]
Wagner et al.

[11] Patent Number: 5,624,464
[45] Date of Patent: Apr. 29, 1997

[54] ARTIFICIAL ACETABULUM

[75] Inventors: Heinz Wagner, Schwarzenbruck, Germany; Roland Willi, Neftenbach; Heinrich Stutz, Frauenfeld, both of Switzerland

[73] Assignees: Sulzer Medizinaltechnik AG, Winterthur; Protek AG, Muensingen-Bern, both of Switzerland

[21] Appl. No.: 489,862

[22] Filed: Jun. 13, 1995

[30]    Foreign Application Priority Data

Jun. 15, 1994 [EP]  European Pat. Off. .............. 94810353

[51] Int. Cl.$^6$ ........................................ A61F 2/32
[52] U.S. Cl. .............................. 623/22; 403/343
[58] Field of Search ............... 623/22, 18, 23; 403/343

[56]         References Cited
U.S. PATENT DOCUMENTS

| | | | |
|---|---|---|---|
| 4,871,368 | 10/1989 | Wagner | 623/22 |
| 4,919,677 | 4/1990 | Stuhmer | 623/22 |
| 5,092,897 | 3/1992 | Forte | 623/22 |
| 5,222,984 | 6/1993 | Forte | 623/22 |
| 5,314,490 | 5/1994 | Wagner | 623/22 |
| 5,458,649 | 10/1995 | Spotorno | 623/22 |

FOREIGN PATENT DOCUMENTS

| | | |
|---|---|---|
| 0237751 | 9/1987 | European Pat. Off. . |
| 0239485 | 9/1987 | European Pat. Off. . |
| 0242633 | 10/1987 | European Pat. Off. . |
| 0265712 | 5/1988 | European Pat. Off. . |
| 0563503 | 10/1993 | European Pat. Off. . |
| WO92/22265 | 12/1992 | WIPO . |

Primary Examiner—Michael J. Milano
Attorney, Agent, or Firm—Townsend and Townsend and Crew LLP

[57]              ABSTRACT

The acetabulum (1) comprises a semispherical support shell (2d) whose inner surface (20) has at least three retaining means (2b) which protrude into the interior. Furthermore, the acetabulum (1) comprises a semispherical inner shell (3) which can be inserted into the correspondingly dimensioned semispherical support shell (2d). The outer surface (30) of the inner shell (3) has at least one recess (3b) extending in a helical manner, in such a way that the inner shell (3) can be rotated into the support shell (2d) with a screw motion, thereby resulting in operative connection between the protruding retaining means (2b) of the support shell (2d) and the recess (3b) extending in a helical manner of the inner shell (3), so that the inner shell (3) is retained in the support shell (2d).

22 Claims, 3 Drawing Sheets

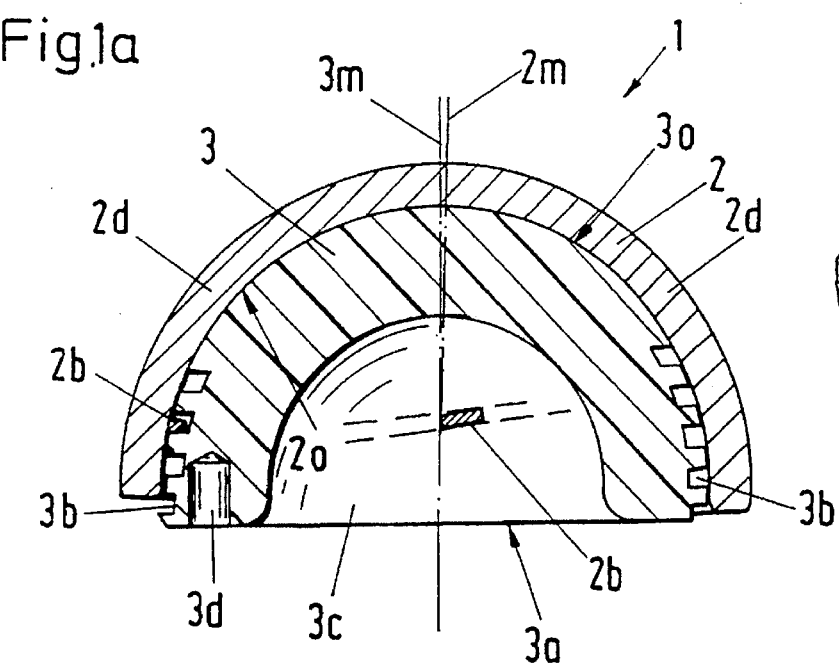
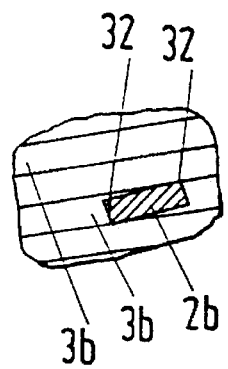
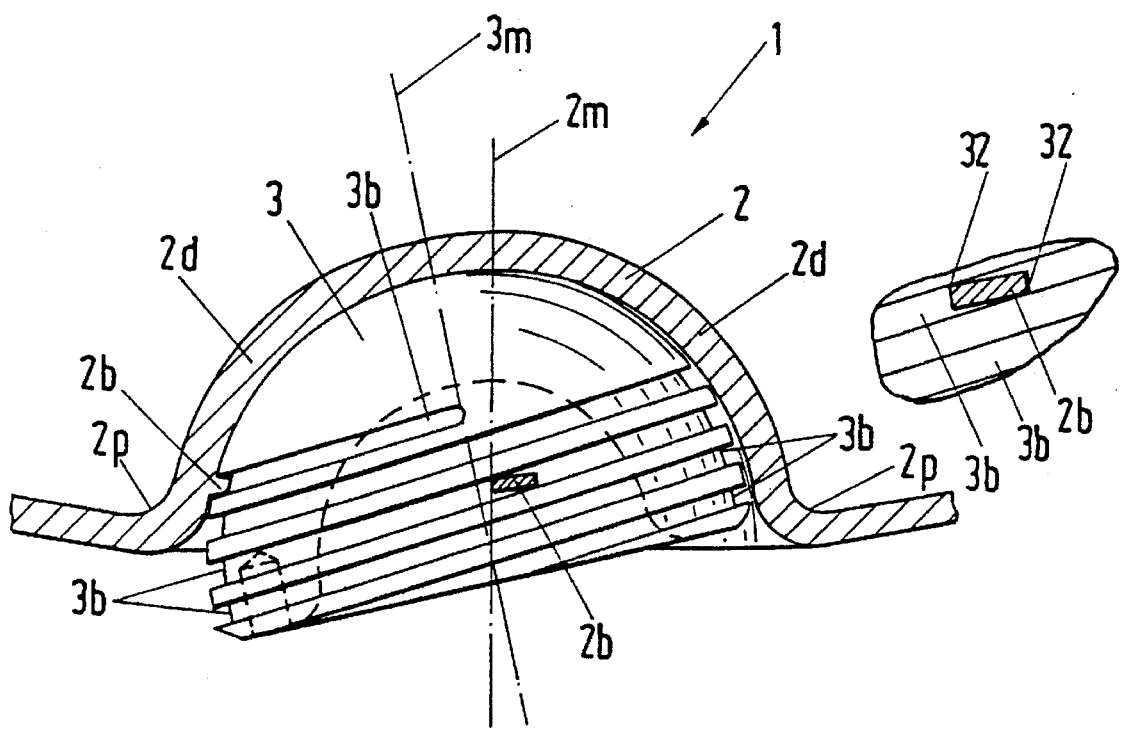

Fig.3
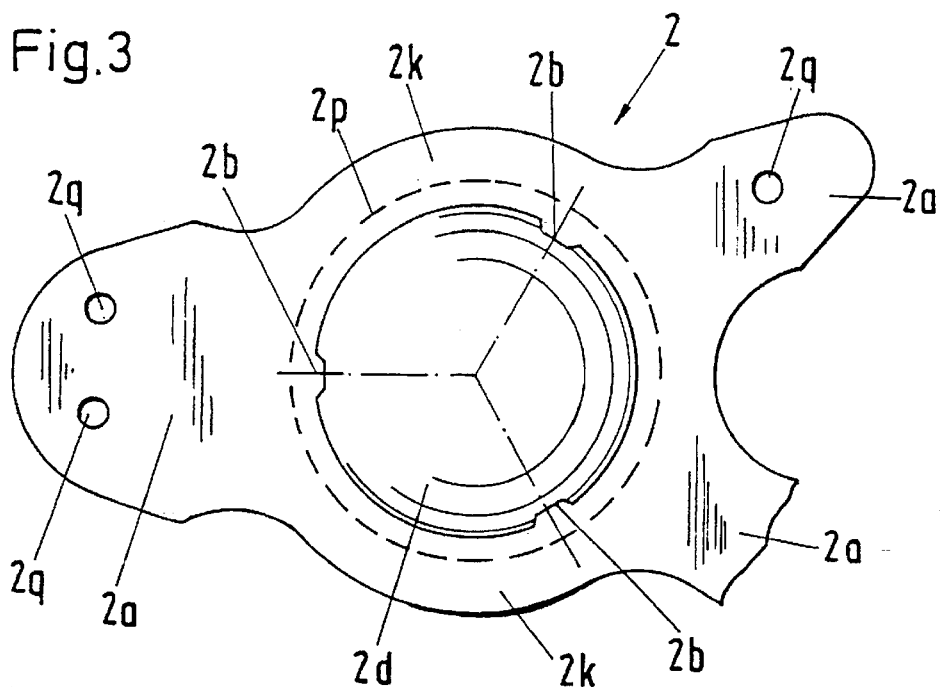
Fig.4
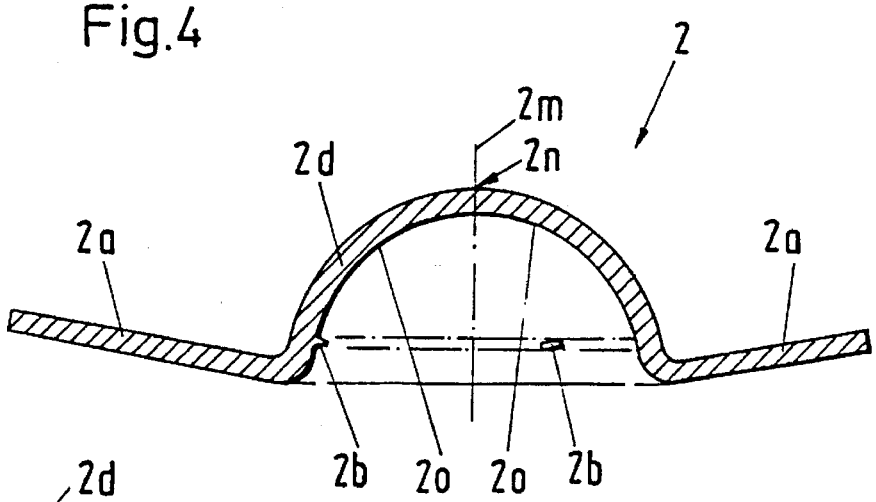
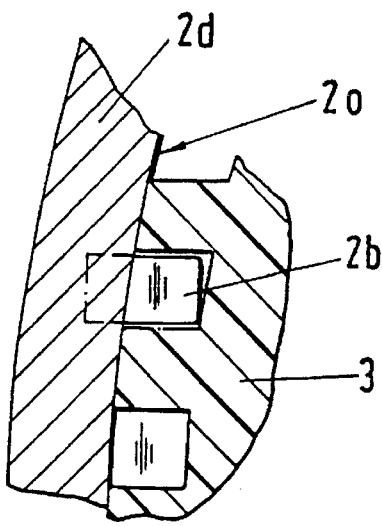
Fig.5

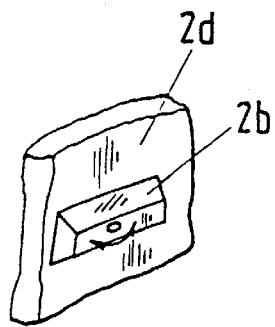
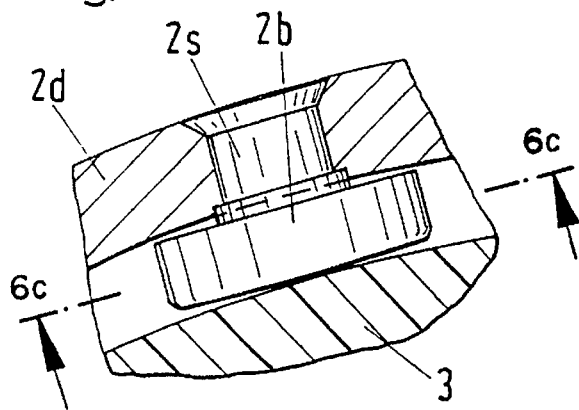
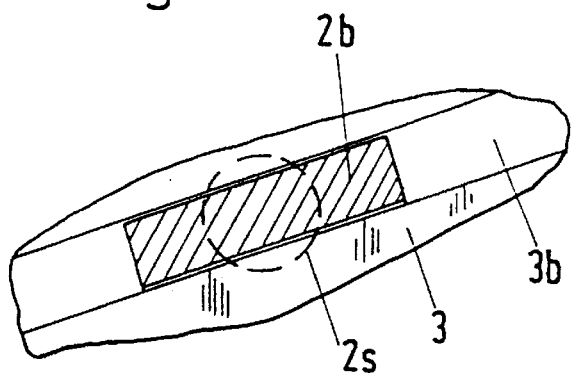
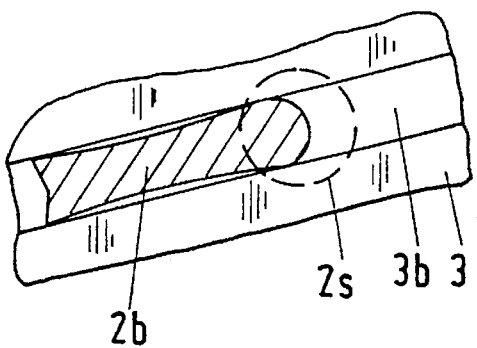
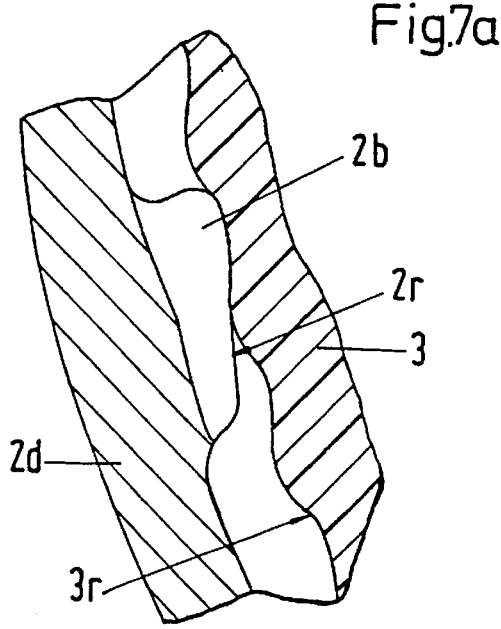
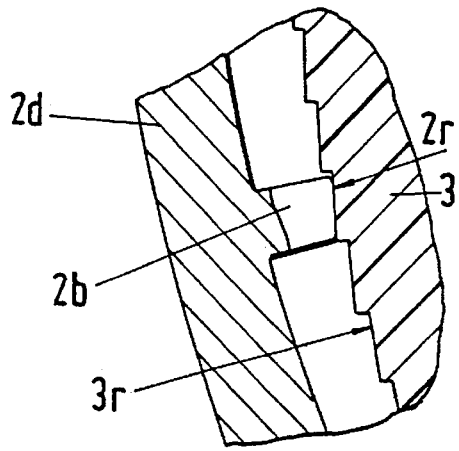

ARTIFICIAL ACETABULUM

BACKGROUND OF THE INVENTION

The invention relates to an artificial acetabulum made of inner and outer shells.

The invention further relates to a method for the assembly and the alignment of the acetabulum in accordance with the invention.

EP-A-0 563 503 discloses a support device for an artificial acetabulum which comprises a semispherical support shell having support tabs with openings at the equatorial edge of the support shell. Such a support device is preferably implanted when the pelvic bone is damaged or severely deteriorated at the region which is to carry the hip joint, which in particular is often the case for reoperations. The support tabs are adapted to the shape of the pelvic bone by plastic deformation during the implantation, so that the support device can be anchored in regions of the pelvic bone capable of bearing a load with bone screws extending through the support tabs. Then a bone cement is applied which fills the clearance between the support shell and the bone tissue and which forms a cement bed within the support shell. Furthermore, an inner shell is set in the support shell, wherein the inner shell is positioned in an orthopedically favourable position, and the mutual position is fixed by the hardening of the bone cement. A disadvantage of such an acetabulum is that a bone cement is necessary for the attachment and alignment of the inner shell. It is known that the use of bone cement has several disadvantages, among other things the disadvantage that the pelvic bone is excessively damaged in unfavorable cases during a reoperation.

SUMMARY OF THE INVENTION

The object of the invention is to provide an acetabulum which is implantable without bone cement, wherein the mutual position of the support shell and the inner shell is fixable during the implantation.

An acetabulum made in accordance with the invention comprises a semispherical support shell whose inner surface has at least three retaining means projecting into the interior. Furthermore, the acetabulum comprises a semispherical inner shell which can be set in the correspondingly dimensioned semispherical support shell. The outer surface of the inner shell has at least one recess extending in a helical manner in such a way that the inner shell is rotatable into the support shell with a rotational screw motion. This establishes an operative connection between the projecting retaining means of the support shell and the helically extending recess of the inner shell, so that the inner shell is held in the support shell.

Advantages of the invention are that the inner shell and the support shell are connectable with different, adjustable angles of inclination, that the connection requires no bone cement, and that the connection is also possible during the implantation with a simple rotational screw motion, so that the angle of inclination is still adjustable or correctable even during the implantation.

BRIEF DESCRIPTION OF THE DRAWINGS

FIG. 1a is a longitudinal section through an artificial acetabulum made according to the present invention;

FIG. 1b is a partial side view of the inner shell shown in FIG. 1a and illustrates the position of the retaining means;

FIG. 2a is a longitudinal section through an outer support shell with of an inserted inner shell;

FIG. 2b is a partial side view of the inner shell shown in FIG. 2a and illustrates the position of the retaining means;

FIG. 3 is a plan view of an outer support shell;

FIG. 4 is a longitudinal section through an outer support shell;

FIG. 5 shows an embodiment of a retaining means;

FIG. 6a–d embodiments of pivotable retaining means;

FIGS. 7a–b shows embodiments of devices providing security against rotation.

DESCRIPTION OF THE PREFERRED EMBODIMENTS

FIG. 1a shows an acetabulum 1 which comprises an outer support device 2 formed as a semispherical support shell 2d with an axis 2m, and a semispherical inner shell 3 with an axis 3m. The inner surface 20 of the support shell 2d has three retaining means 2b which project into the interior of the support shell 2d. FIG. 1a shows the arrangement of the retaining means 2b. The outer surface 30 of the inner shell 3 has a recess 3b extending in a helical manner. When the outer shell 2b is brought together with the inner shell 3, the mutual position of the axes 2m, 3m is adjustable over a wide range by first positioning the inner shell 3 in a desired position related to the support shell 2b and then rotating the inner shell 3 into the support shell 2b by a rotational movement about the axis 2m, wherein the recess 3b formed in a helical manner engages with the retaining means 2b, so that a mutually operative connection results. In the embodiment shown, the inner shell 3 is entirely rotated into the support shell 2b, so that the inner surface 20 of the support shell 2b lies on the outer surface 30 of the inner shell 3 in a prestressed manner, which results in a reaction force which extends in the direction of the axis 3m and which is absorbed by the retaining means 2b, so that the inner shell 3 is firmly arrested in the support shell 2d. In the present embodiment, the retaining means 2b as shown in FIG. 1b with a plan view on the outer surface 30 is shaped as a rectangle in cross-section, which extends slightly offset with respect to the shape of the recess 3b, so that very small contact surfaces 32 result between the inner shell 3 and the support shell 2d. The resulting high surface strain provides security against a rotation of the two shells 3, 2d by, for example, forming the retaining means 2b from a metal and the inner shell 3 from a plastic such as polyethylene, so that the retaining means 2b digs itself into the plastic at the contact surface 32 and plastically deforms the inner shell 3, which obstructs or prevents a mutual rotation of the shells 3, 2d.

The inner shell 3 has a circular aperture 3a and a spherical interior 3c for the accommodation of a ball-and-socket joint head. Furthermore, the inner shell 3 has a recess 3d for the accommodation of a setting tool for rotationally moving the inner shell 3 into the support shell 2d. The support shell 2d shown is fixable at the pelvic bone via bone screws; the corresponding recesses in the support shell 2d are however not shown.

FIGS. 2, 3 and 4 show a further embodiment of a metallic support device 2 having a semispherical support shell 2d and projecting support tabs 2a at its equatorial edge. As mentioned in the introduction of the specification, such a support device 2 is fastened to the pelvic bone with bone screws extending through apertures 2q in the support tabs 2a. Depending on the condition of the pelvic bone, it is possible that the alignment of the support shell 2d can move into an orthopedically unfavorable position. This can be corrected by thereafter securing the inner shell 3 in an orthopedically favorable position in the support shell 2d. Such a procedure during the implantation has the advantage that an operator can fasten the support device 2 to the pelvic bone in an optimum manner in a first step, since there is a large tolerance with respect to the alignment of the support device 2, and that the inner shell 3 is orthopedically favorably aligned in a second step. FIG. 2a shows an acetabulum 1, whose axis 3m of the inner shell 3 has a relatively divergence from the axis 2m of the support shell 2d. The inner shell 3 is shown in a side view and the outer surface 3θ has a single recess 3b extending in a spiral manner. In FIG. 2b, the cooperation of the retaining means 2b with the recess 3b is shown. Small contact surfaces 32 result again from the form and arrangement of the retaining means 2b.

The plan view of the metallic support device 2 in accordance with FIG. 3 shows the three retaining means 2b equally distributed about the perimeter in the region of the equatorial edge 2p, and protruding into the interior of the support shell 2d. In the side view in FIG. 4, it can be seen that the retaining means 2b are arranged in a plane, wherein the alignment of the individual retaining means 2b has an angle of inclination with respect to this plane. The retaining means 2b have the purpose to engage with a recess 3b of the inner shell 3 in order to retain it, wherein the inner shell 3 should be insertable into the support shell 2d in a plurality of positions. To satisfy this purpose, there are a plurality of advantageous possible arrangements of the retaining means 2b within the inner surface 20. It can be advantageous as well to arrange more than three retaining means 2b at the inner surface 20. In addition, there are a plurality of possibilities for the form of the retaining means 2b in order to satisfy the required purpose. FIG. 5 shows a cross-section through an inner shell 3 and a support shell 2b with a further embodiment of a retaining means 2b. The retaining means 2b is formed as a cylindrically shaped body embedded in a corresponding fitted recess at the inner surface 20 of the support shell 2d. The inner surface 20 of the support shell 2d can have a plurality of recesses for a retaining means 2b, so that the retaining means 2b can also be arranged at the support shell 2d immediately before or during the implantation. Thereby the mutual position of the support shell 2d and the inner shell 3 can be influenced in a more differentiated manner.

FIGS. 6a to 6d show further embodiments of retaining means 2b which all have the characteristic, as shown in FIG. 6a by an arrow, of being rotatably mounted at the support shell 2d, so that the alignment of the retaining means 2b conforms to the shape of the recess 3b of the inner shell 3. FIG. 6b shows a section through a rotatably mounted retaining means 2b having a cylindrical part 2s which lies in an aperture of the support shell 2d and which thereby is rotatable with respect to the support shell 2d. Furthermore, the position of the inner shell 3 is shown. A section along line A—A is shown in FIG. 6c, from which it can be seen that the retaining means 2b is symmetrically formed and adapts its position to the shape of the recess 3b. FIG. 6d is a view similar to FIG. 6c and shows a further embodiment of a retaining means 2b which is asymmetrically connected to the cylindrical part 2s defining the center of rotation. The end of the retaining means 2b which is opposite from the part 2s is formed in the manner of a swallowtail and has two distinctive edges. These edges can serve as a security against a rotation of the inner shell 3. In the case of the inner shell 3 rotating back, one or both edges of the retaining means 2b can dig into the inner shell 3, thus resulting in a security against rotation. An asymmetrical form of the retaining means 2b promotes the behavior of the retaining means to dig into the inner shell 3 during the back-rotation.

FIGS. 7a and 7b show a section through a support shell 2d with retaining means 2b and an inner shell 3. The shape of the surface 2r of the retaining means 2b and the surface 3r of the inner shell 3 are matched to each other so that a rotation of the support shell 2d relative to the inner shell 3 is generally prevented in order to form a security against rotation. In FIG. 7a, the surface 3r has a wave shape which is formed in such a way with respect to the surface 2r that a rotation is prevented, but is possible by applying a relatively larger torque. FIG. 7b shows a surface 3r formed with a saw-tooth formation into which the correspondingly formed retaining means 2b engages. With this embodiment, an inner shell 3 can be non-releasably connected with a support shell 2d. By applying a very large torque, the inner shell 3 can be released but surface 3r of the inner shell 3 would be partially destroyed thereby.

What is claimed is:

1. Artificial acetabulum, comprising a support shell and an inner shell which can be inserted therein, the support shell including a semispherical inner surface having at least three projecting retaining means arranged to lie in one plane, the inner shell including a semispherical outer surface having at least one recess extending in a helical manner so that the inner shell can be inserted into the support shell with a screw motion in order to bring the retaining means and the recess into an operative connection and to fix the mutual positions of the support shell and the inner shell.

2. Artificial acetabulum in accordance with claim 1 wherein all retaining means are arranged in a plane which is perpendicular to an axis of the support shell.

3. Artificial acetabulum in accordance with claim 1 wherein the retaining means is formed as a cam.

4. Artificial acetabulum in accordance with claim 3 wherein the inner surface of the support shell has recesses for accommodating a retaining means formed in the manner of a cam.

5. Artificial acetabulum in accordance with claim 1 wherein the retaining means and the recess have a surface structure formed to prevent relative screw motion in at least one direction of rotation for locking the inner shell in the support shell.

6. Artificial acetabulum accordance with claim 1 wherein the support shell is formed from a metal and the inner shell is formed from one of a metal, a plastic and a ceramic material.

7. Artificial acetabulum comprising a support shell and an inner shell which can be inserted therein, the support shell including a semispherical inner surface having at least three projecting retaining means, the inner shell including a semispherical outer surface having at least one recess extending in a helical manner so that the inner shell can be inserted into the support shell with a screw motion in order to bring the retaining means and the recess into an operative connection and to fix the mutual positions of the support shell and the inner shell, and wherein the retaining means is pivotally connected with the support shell so that the position of the retaining means adapts itself to a course of the recess.

8. Artificial acetabulum in accordance with claim 7 wherein the retaining means has a center of rotation and is formed asymmetrically relative to the center of rotation.

9. An artificial acetabulum comprising a support shell including a concave inner surface and at least three spaced-apart retaining members projecting inwardly from the inner surface, all retaining members together extending over a minor portion of a circumference of the inner side and being arranged to lie in one plane; and an inner shell having a convex outer surface which can be inserted into the support shell, the outer surface including a hetically formed recess adapted to be simultaneously engaged by the retaining members so that the inner shell can be inserted into the support shell by turning the recess along the projecting members to form an operative connection between the shells and to fix the relative positions of the support shell and the inner shell.

10. An artificial acetabulum according to claim 9 wherein the concave and convex surfaces are spherical surfaces.

11. An artificial acetabulum according to claim 9 wherein the retaining members have equal lengths in the direction of the circumference.

12. An artificial acetabulum according to claim 11 wherein the retaining members are equally spaced.

13. An artificial acetabulum according to claim 9 wherein the retaining members lie on a common imaginary line on the concave inner surface of the support shell.

14. An artificial acetabulum according to claim 13 wherein the retaining members have a length in the direction of the line and are angularly inclined relative to the line.

15. An artificial acetabulum comprising a support shell including a concave inner surface and at least three retaining members projecting inwardly from the inner surface and lying on a common imaginary line extending along the inner surface, each retaining member having a length in a direction of the imaginary line which defines a relatively small angle with respect to a plane which is perpendicular to a polar axis through the outer shell, the length of the retaining members being significantly shorter than a spacing between the retaining members; and an inner shell inserted into the outer shell including a convex outer surface having a helically arranged recess engaging the at least three retaining members for insertion of the outer shell into the inner shell by rotating the two with respect to each other while the retaining members are engaged by the recess; whereby the relative angular positions of the polar axes of the support shell and the outer shell are changeable by varying an angular inclination of the recess relative to the polar axis of the support shell before the retaining members are engaged by the recess and the inner shell is rotated into the support shell.

16. Artificial acetabulum in accordance with claim 15 wherein the inner shell has a semispherical outer surface and the support shell has a semispherical inner surface.

17. Artificial acetabulum in accordance with claim 5 wherein all retaining means are arranged to lie in one plane.

18. An artificial acetabulum according to claim 15 wherein the imaginary line is perpendicular to the polar axis.

19. An artificial acetabulum according to claim 18 including mounting tabs projecting away from an outer surface of the support shell and having means for securing the tabs to bone.

20. An artificial acetabulum according to claim 15 wherein the imaginary line is slightly angularly inclined relative to the plane which is perpendicular to the polar axis.

21. An artificial acetabulum comprising a support shell including a concave inner surface and at least three retaining members projecting inwardly from the inner surface, each retaining member having a length in a general direction of a circumference of the inner surface which defines a relatively small angle with respect to a plane which is perpendicular to a polar axis through the outer shell, a portion of the at least three retaining members being further disposed in a common plane which is perpendicular to the polar axis; and an inner shell inserted into the outer shell including a convex outer surface having a helically arranged recess engaging the at least three retaining members for insertion of the outer shell into the inner shell by rotating the two with respect to each other while the retaining members are engaged by the recess; whereby the relative angular positions of the polar axis of the support shell and a polar axis of the outer shell are changeable by varying an angular inclination of the recess relative to the polar axis of the support shell before the retaining members are engaged by the recess and the inner shell is rotated into the support shell.

22. An artificial acetabulum according to claim 21 including a plurality of mounting tabs extending from the support shell generally transversely to its polar axis and having means for attaching the tabs to a supporting bone.

* * * * *